United States Patent
Guillot et al.

(10) Patent No.: US 10,792,134 B2
(45) Date of Patent: Oct. 6, 2020

(54) METHOD AND DEVICE FOR MANUFACTURING AND CONTROLLING THE CONFORMITY OF A DENTAL PROSTHESIS FROM PARAMETERS OBTAINED WITH A SHADE SELECTING DEVICE

(71) Applicant: TCM, Limoges (FR)

(72) Inventors: Julien Guillot, Limoges (FR); Frédérik Rougier, Thouron (FR)

(73) Assignee: TCM (FR)

( * ) Notice: Subject to any disclaimer, the term of this patent is extended or adjusted under 35 U.S.C. 154(b) by 0 days.

(21) Appl. No.: 15/854,077

(22) Filed: Dec. 26, 2017

(65) Prior Publication Data

US 2018/0161132 A1    Jun. 14, 2018

Related U.S. Application Data

(62) Division of application No. 14/837,449, filed on Aug. 27, 2015, now abandoned.

(30) Foreign Application Priority Data

Jun. 30, 2015 (FR) .................................. 15 56140
Jun. 30, 2015 (FR) .................................. 15 56141

(51) Int. Cl.
*A61C 13/08* (2006.01)
*A61B 5/00* (2006.01)
(Continued)

(52) U.S. Cl.
CPC .......... *A61C 13/082* (2013.01); *A61B 5/0013* (2013.01); *A61B 5/0088* (2013.01);
(Continued)

(58) Field of Classification Search
CPC ...... G01J 3/508; A61B 5/0088; A61B 5/0013; A61B 5/1032; A61B 2576/02
See application file for complete search history.

(56) References Cited

U.S. PATENT DOCUMENTS 1,384,513 A    7/1921  Busby
1,548,238 A    8/1925  Adams
(Continued)

FOREIGN PATENT DOCUMENTS

WO    9901746 A1    1/1999
WO    2008036644 A1    3/2008

OTHER PUBLICATIONS

French Search Report for FR Application No. 1556140, dated May 27, 2016.
(Continued)

*Primary Examiner* — Vincent H Tran
(74) *Attorney, Agent, or Firm* — Lerner, David, Littenberg, Krumholz & Mentlik, LLP

(57) ABSTRACT

A device for tooth shade measurement comprising a housing, a handle and a measuring head, characterized in that said measuring head includes a hollow body extending along a longitudinal axis, said hollow body comprising a proximal end, a bent distal end relative to the longitudinal axis, said distal end being provided with a removable tip designed to come into contact with a tooth surface to be analyzed, at least one light source and image acquisition means, integral with the hollow body, said hollow body being adapted to transmit the light from said light source from the proximal end up to the distal end, and in that said device comprises an orientation assembly for mounting the proximal end of the hollow body in the housing so that the measuring head occupies different angular positions relative to the housing.

4 Claims, 6 Drawing Sheets

(51) Int. Cl.
   *A61C 1/08* (2006.01)
   *G01J 3/50* (2006.01)
   *A61B 5/103* (2006.01)

(52) U.S. Cl.
   CPC .............. *A61C 1/088* (2013.01); *G01J 3/508* (2013.01); *A61B 5/0022* (2013.01); *A61B 5/1032* (2013.01); *A61B 2576/02* (2013.01)

(56) References Cited

U.S. PATENT DOCUMENTS

| | | | |
|---|---|---|---|
| 2,542,038 | A | 2/1950 | Lewis |
| 4,564,354 | A | 1/1986 | Rosenstatter |
| 6,038,024 | A * | 3/2000 | Berner ............... G01J 3/02 356/326 |
| 6,157,454 | A | 12/2000 | Wagner et al. |
| 6,190,170 | B1 * | 2/2001 | Morris ............... A61C 19/10 433/203.1 |
| 6,249,348 | B1 | 6/2001 | Jung et al. |
| 6,328,567 | B1 * | 12/2001 | Morris ............... A61C 19/10 433/203.1 |
| 6,540,513 | B2 * | 4/2003 | Berner ............... A61C 19/10 433/26 |
| 6,750,971 | B2 | 6/2004 | Overbeck et al. |
| 6,870,616 | B2 | 3/2005 | Jung et al. |
| 7,234,937 | B2 * | 6/2007 | Sachdeva ............. A61C 7/00 433/24 |
| 8,040,514 | B2 * | 10/2011 | Kobayashi ........... A61C 19/10 356/244 |
| 10,299,891 | B2 * | 5/2019 | Lemchen ............. G06F 19/328 |
| 2002/0012895 | A1 | 1/2002 | Lehmann |
| 2002/0021439 | A1 * | 2/2002 | Priestley ............ G01J 3/46 356/243.5 |
| 2002/0171824 | A1 | 11/2002 | Overbeck et al. |
| 2003/0156283 | A1 | 8/2003 | Jung et al. |
| 2003/0207228 | A1 | 11/2003 | Lehmann et al. |
| 2004/0252303 | A1 * | 12/2004 | Giorgianni .......... G01J 3/50 356/402 |
| 2005/0037314 | A1 * | 2/2005 | Morris .............. A61C 19/10 433/26 |
| 2005/0129453 | A1 | 6/2005 | Bravo-Loubriel |
| 2006/0139644 | A1 | 6/2006 | Kahn et al. |
| 2007/0212667 | A1 | 9/2007 | Jung et al. |
| 2008/0063998 | A1 | 3/2008 | Liang et al. |
| 2009/0133260 | A1 * | 5/2009 | Durbin ............. A61C 13/0004 29/896.11 |
| 2009/0168063 | A1 * | 7/2009 | Kobayashi .......... A61C 19/10 356/404 |
| 2010/0076581 | A1 * | 3/2010 | Violante ........... A61C 13/0004 700/98 |
| 2011/0171604 | A1 * | 7/2011 | Durbin ............. A61C 9/0053 433/213 |
| 2012/0179492 | A1 * | 7/2012 | Rhodes ............. G06Q 50/22 705/3 |
| 2013/0096457 | A1 | 4/2013 | Qiu et al. |
| 2014/0030670 | A1 * | 1/2014 | Wong ............... G01J 3/46 433/29 |
| 2014/0095200 | A1 * | 4/2014 | Bostock ............ A61C 13/00 705/3 |
| 2015/0374460 | A1 * | 12/2015 | Sachdeva .......... G06T 17/00 703/1 |

OTHER PUBLICATIONS

French Search Report for FR Application No. 1556141, dated Apr. 13, 2016.

* cited by examiner

METHOD AND DEVICE FOR MANUFACTURING AND CONTROLLING THE CONFORMITY OF A DENTAL PROSTHESIS FROM PARAMETERS OBTAINED WITH A SHADE SELECTING DEVICE

CROSS-REFERENCE TO RELATED APPLICATIONS

This application is a divisional of U.S. patent application Ser. No. 14/837,449 filed on Aug. 27, 2015, which claims priority under 35 USC 119(a) to French Patent Application No. 1556140 filed on Jun. 30, 2015, and French Patent Application No. 1556141 filed on Jun. 30, 2015, the disclosures of which are incorporated herein by reference.

BACKGROUND OF THE INVENTION

The present invention relates to a method and a device for manufacturing and controlling the conformity of a dental prosthesis from parameters taken intra-orally with a shade selecting device.

We know that the manufacture of dental prostheses is performed by dental technicians who are not necessarily in the vicinity of the dental practitioner's office, and can even take place in industrially oriented units in countries which are geographically quite distant from the site where they will be seated but whose labor costs are lower.

The prosthesis thus remotely manufactured is sent by courier to the dental practitioner and it is necessary to deliver a prosthesis that is not only dimensionally accurate, this not being the object of the present invention, but also aesthetically perfect. It is indeed essential for a prosthesis: to be natural to the point that it is not noticed and fits perfectly. The shade in the broad sense is therefore paramount and additional information allows achieving optimal results.

This is where the problems arise because it is necessary to determine parameters, not only subjectively, but also through actual, repeatable and verifiable measurements.

Then, once these parameters are determined, it is necessary to verify that the prosthesis, once manufactured, is in conformity with these parameters so as not to deliver a prosthesis that would not fit. Poor workmanship results in significant costs because it entails:

- discovering the defect intra-orally, which incurs expenses because it requires an unnecessary trip for the client and unnecessary work for the practitioner,
- manufacturing a new prosthesis resulting in a delay and associated cost,
- sending said new prosthesis also resulting in a delay and associated cost,
- asking the client to come back, and
- working to seat the new prosthesis, which requires time and is therefore costly, not counting the time spent to exchange information and the negative impact on the reputation of the practitioner.

It is imperative to ensure quality control upstream of the installation, from the time of manufacture, so that the practitioner is guaranteed to receive a prosthesis ready to be seated, in conformity with the parameters established during the shade selection.

The first difficulty is precisely the shade selection. Shade selection entails recording a set of tooth features that aims to bring about in the most faithful way possible the appearance of the tooth. The tooth shade corresponds to the color of the tooth, that is to say, brightness, saturation, hue, but may also incorporate any parameter that has an effect on the appearance of the tooth such as its translucency or transparency, or even its surface condition.

When manufacturing a dental prosthesis, the prosthesis must exactly match the colors of the neighboring teeth, or as close as possible, in order to go unnoticed in the patient's mouth.

According to a known technique, the evaluation of the shade of a tooth can be done visually by a dentist. The dentist performs the shade selection for manufacturing the dental prosthesis by comparing the patient's tooth to teeth in a reference color chart. Once the shades are determined, they are communicated to a dental technician to enable him to choose the pulp mixtures to be used in the manufacture of the corresponding prosthesis. This measurement technique is unreliable. The evaluation of the shade of a tooth is subjective and can vary from one practitioner to another because of the perception of the eye mechanism. This measure is also influenced by environmental factors such as the lighting conditions.

To overcome the practitioner's perception errors, a more objective evaluation of a tooth can be performed under a light beam using a spectrum analyzer. Such a device comprises a handle and a measuring head coming into contact with the tooth to be measured, the measuring head being connected to the emission-reception means by a fiber optic bundle. The handle comprises a light source such as light-emitting diodes (LEDs) and the measuring head comprises light sensors. However, this device can only make spot measurements on the tooth.

According to another form of execution, it is also possible to use an imaging device for performing a mapping of the tooth. The captured image is then subjected to image processing such as automatic segmentation to determine a set of characteristics of the tooth. Such a shooting device comprises a measuring head and a handle. The head includes at least an image sensor, an optical system and an LED lighting system for illuminating the shooting area. Although it can perform a two-dimensional measurement, this device has a relatively bulky measuring head.

Another drawback of these known devices is related to the fact that the measuring head remains stationary relative to the handle. Therefore, the use of these devices is limited to a front portion of the patient's dental arch.

Also, even though the devices of the prior art may be used for implementing the method according to the invention, the device described below for implementing the method according to the present invention achieves a better result. This device aims to overcome the disadvantages of the prior art by providing a device with a very compact measuring head which allows performing a two-dimensional analysis while having access to all the teeth in the mouth. The method for manufacturing and controlling is consequently optimized.

BRIEF SUMMARY OF THE INVENTION

For this purpose, the tooth shade measuring device includes a housing, a handle and a measuring head, said measuring head comprising:

- a hollow body extending along a longitudinal axis, said hollow body comprising a proximal end, a distal end bent relative to the longitudinal axis, said distal end being provided with a removable tip intended to come into contact with the tooth surface to be analyzed;
- at least one light source and image acquiring means integral with the hollow body, said hollow body being adapted to transmit light from said light source from the proximal end to the distal end;

and said device comprising an orientation assembly for mounting the proximal end of the hollow body in the housing so that the measuring head occupies different angular positions relative to the housing.

According to one embodiment of the device, the orientation assembly comprises at least a first half-shell suitable to be assembled to a second half-shell to form a hollow shell defining a cavity configured to receive said proximal end, said cavity having on its inner surface a radially projecting surface intended to cooperate with a plurality of slots having a complementary shape formed on the outer surface of the proximal end to ensure the different angular positions of the measuring head relative to the housing.

Advantageously, the orientation assembly comprises a locking means for locking the measuring head in a defined angular position relative to the housing.

It is therefore understandable that the shade selection, when focusing on the patient's tooth and limiting the interactions of adjacent teeth, overcomes the impact of the whole environment of the tooth concerned.

Thus, as the shade selection is well focused thanks to the device, and as this shade selection overcomes the environment, the parameters measured and transmitted to the dental technician and/or the laboratory will be subsequently perfectly matched and allow adequate control since the prosthesis, while in its place of manufacture, is precisely not in its environment.

BRIEF DESCRIPTION OF THE DRAWINGS

Other features and advantages of the method according to the present invention will appear from the following description of particular embodiments, given as nonlimiting examples, as well as from the description of the device used, this with reference to the accompanying drawings, in which.

DETAILED DESCRIPTION

Figure 1:
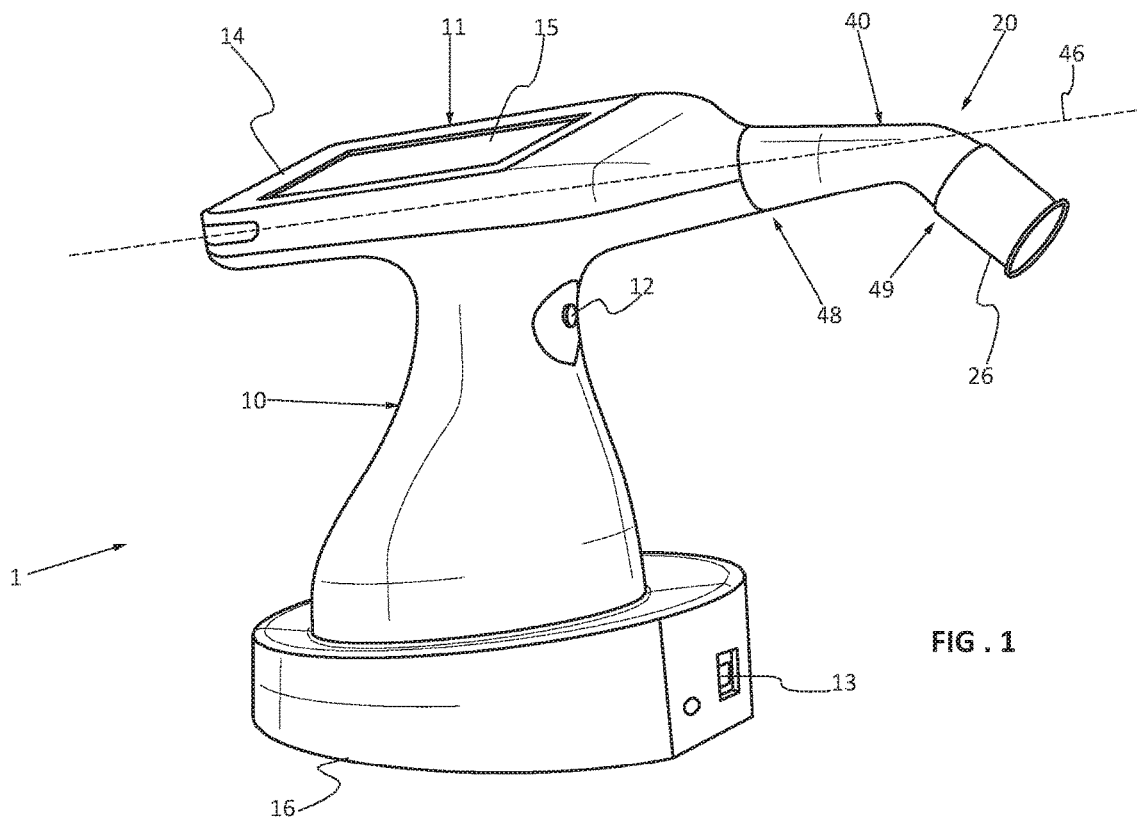
FIG. 1 is a schematic perspective view of a shade selecting device according to an embodiment.
Figure 2:
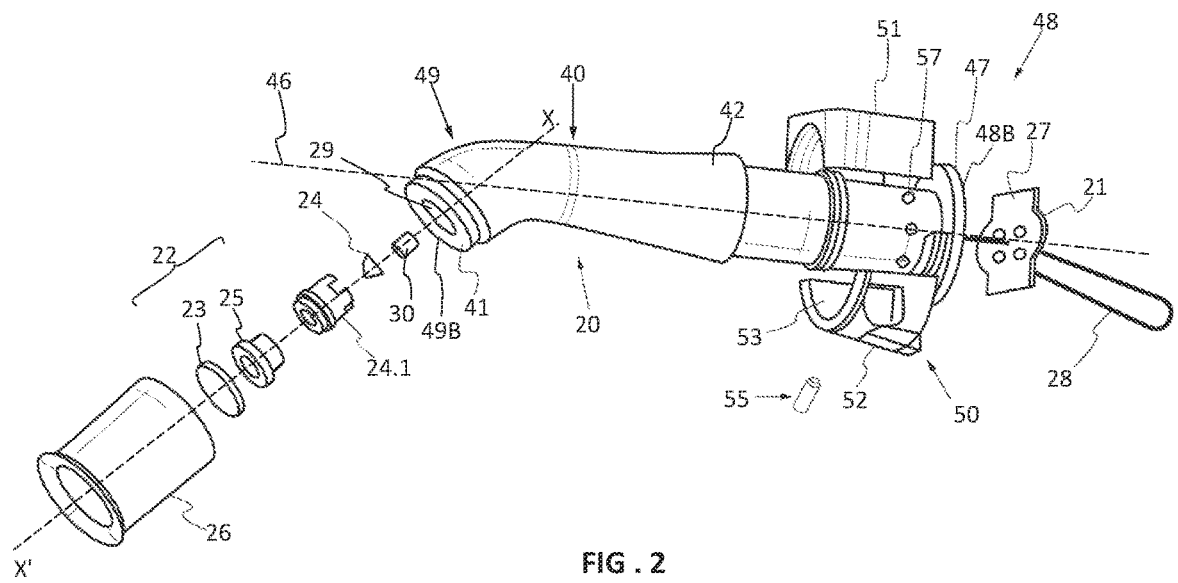
FIG. 2 is an exploded perspective view of the measuring head of the device of FIG. 1.

FIG. 1 shows in 1 a measuring device for acquiring a color image of a tooth or the spectral data of a tooth. These measures allow achieving a complete and precise mapping of the variations in the different characteristics of the tooth. In particular, this mapping allows determining the tooth shade for the realization of a dental prosthesis according to the method of the present invention.

The device comprises a gripping handle 10 topped by a housing 11, one end of the housing 11 being provided with a measuring head 20 for acquiring spectral data or images.

According to one embodiment, the housing 11 has a substantially parallelepipedic shape with an upper face 14 comprising a display 15 which is used to indicate in real time the data relating to the analyzed tooth generated by the measuring head 20.

These data can then be transmitted to the computer means of the user by Wi-Fi connection or through a USB connection to be processed by a calculation software for processing the images. In this case, the data is transmitted to a computer station accessible by the practitioner who performed said measure in order to integrate these data in the client's record.

According to a particularly advantageous embodiment, the calculation unit is integrated directly into the housing 11 that allows displaying the color map of the analyzed tooth. In this case, the processed data are stored directly on the computer station of the practitioner.

Computer station means, in the remainder of this description, either a networked workstation or an isolated computer connected to the Internet cloud so as to allow a controlled and secure access to said data by authorized third parties.

According to one embodiment, the device comprises a base 17 for placing the unit on a flat surface. The base 17 also includes a wired USB-type connection 13 for data transfer. Furthermore, the handle 10 comprises a housing for receiving a battery. This battery can be recharged when the device is placed on its base, via a USB connection or via a charger connected to the mains.

The gripping handle 10 further comprises an activation button 12 of the measuring head.

According to an embodiment illustrated in FIGS. 1 to 4, the measuring head 20 comprises a hollow body 40 oriented along a longitudinal axis 46. This hollow body comprises a proximal end 48 mounted to the housing 11 and a bent distal end 49 provided with a removable tip 26 designed to come into contact with the tooth surface to be analyzed. The hollow body 40 also includes a passage 29 which extends from the proximal end 48 to the distal end 49. The extremity 48B of the proximal end 48 and the extremity 49B of the distal end 49 are open.

The measuring head 20 includes at least one light source 21 and image acquisition means, integral to the hollow body 40.

According to a preferred embodiment of the device, said at least one light source is fixed to the extremity 48B of the proximal end 48 of the body 40 and the image acquisition means is fixed to the extremity 49B of the distal end 49 of the body 40. The latter allows transmitting the illumination light from the light source 21 from the proximal end 48 of the body to the distal end 49 of the body to illuminate the tooth surface to be analyzed. The device further comprises a cable 28 for transmitting data extending into the passage 29 of the body from the proximal end 48 of the body to the distal end 49 for transmitting at least one image from the distal end up to the proximal end. This cable connects in particular the acquisition means to a data processing unit.

According to one embodiment, the hollow body 40 consists of an optical waveguide 41 for guiding the illumination light emitted from the light source to a tooth surface, surrounded by an overmolding 42.

According to an important feature, the device includes an orientation assembly 50 for associating the proximal end 48 of the hollow body 40 to the housing 11 so that the measuring head 20 occupies different angular positions relative to the housing. This specific arrangement enables imparting to the device an additional degree of freedom to facilitate access to the teeth of the two dental arches. In addition, being able to guide the measuring head without changing the position and orientation of the handle 10 relative to the tooth surface to be analyzed enhances the usability of the device for the user.

The axis XX' of the distal end 49 of the hollow body 40 is preferably bent at an inclination angle α relative to the longitudinal axis 46 carried by the body 40 to facilitate access of the measuring head to the teeth located in the rear part of the two dental arches. This angle is between 10 and 60°. It is preferably equal to 45°.

Cooperation between the bent distal end 49 of the hollow body 40 and the various angular positions allows positioning the tip 26 so that the longitudinal axis XX' of the tip 26 is always perpendicular to the tooth surface to be analyzed.

The orientation assembly 50 comprises a first half-shell 51 and a second half-shell 52, the two half-shells being assembled to form a hollow shell defining a cavity 53 around the longitudinal axis 46. The two half-shells 51, 52 are held together by known fastening means 61, 62. The proximal end 48 of the hollow body 40 is received in the cavity 53. One of the two half-shells 52 comprises a radially projecting surface 56 designed to cooperate with a plurality of slots having a complementary shape, formed on an outer surface of the proximal end 48 of the hollow body 40 to ensure the different angular positions of the measuring head 20 relative to the housing 11.

Figure 7:
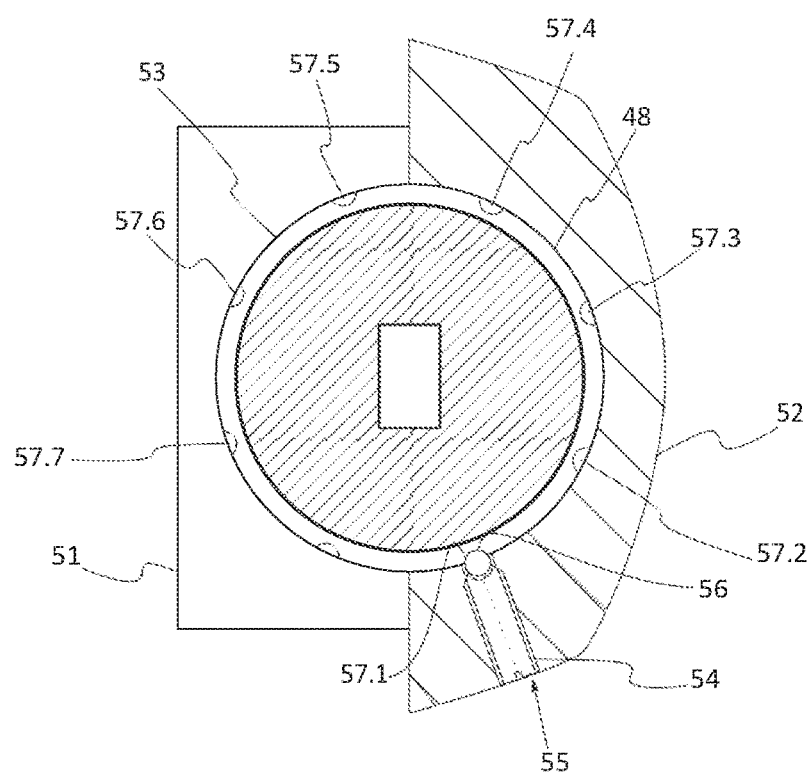
FIG. 7 is a sectional view of the proximal end of the measuring head held between two half-shells of the orientation assembly of the device.

As illustrated in FIG. 7, the proximal end 48, which has a substantially circular cross-section, is housed in the cavity 53 formed by the two half-shells 51, 52. The proximal end 48 has on its outer surface a series of seven slots numbered 57.1 through 57.7. The slots 57.1 to 57.7 are distributed so as to position the measuring head in various angular positions between 0 and 270°. The slots are distributed in such a way that the angular increment between two positions is equal to 45°. In FIG. 7, the measuring head 20 is oriented in an angular position in which the projecting surface 56 is received in the slot 57.1, corresponding for example to a reference angular position equal to 0°. The measuring head 20 is then oriented relative to this reference angular position.

The radially projecting surface, designed to cooperate with one of the slots 57, is formed by a ball screw 55 received in a slot 54 arranged in the wall of one of the half-shells 52 of the orientation assembly. The ball screw 55 comprises at one end facing the interior of the cavity 53, a ball which forms the projecting surface 56 having a shape complementary to that of the slots.

To place the measuring head 20 in a defined angular position, the optical waveguide is made to rotate in order to place the ball in one of the slots.

Advantageously, the ball screw 55 is also a locking means for locking the measuring head in the selected angular position.

In one advantageous embodiment, the proximal end 48 of the body is provided with an abutment which limits the orientation of the measuring head only between 0°, corresponding to the position illustrated in FIG. 7, and 270°. This abutment helps prevent the measuring head from performing complete revolutions, thereby preventing the data transmission cable 28 from twisting.

Figure 4A:
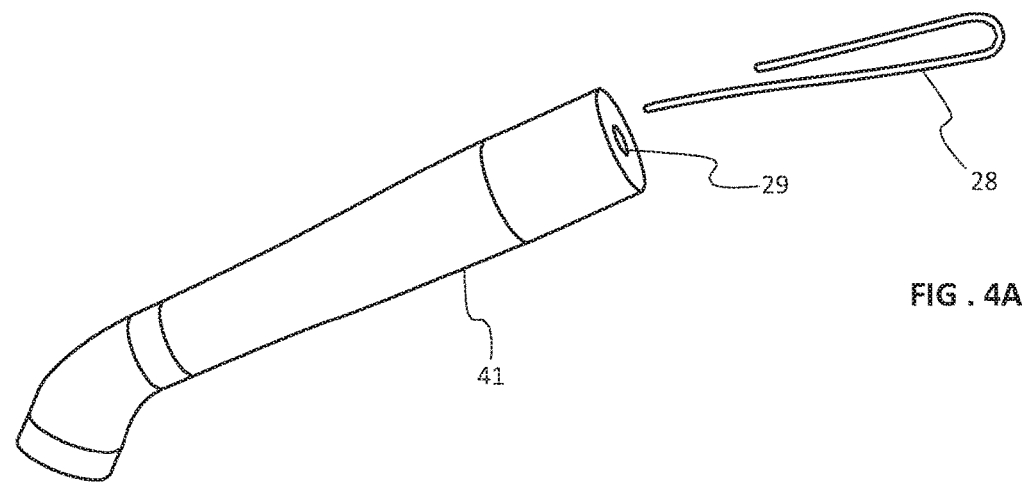
FIG. 4A is a perspective view of the optical waveguide of the measuring head.
Figure 4B:
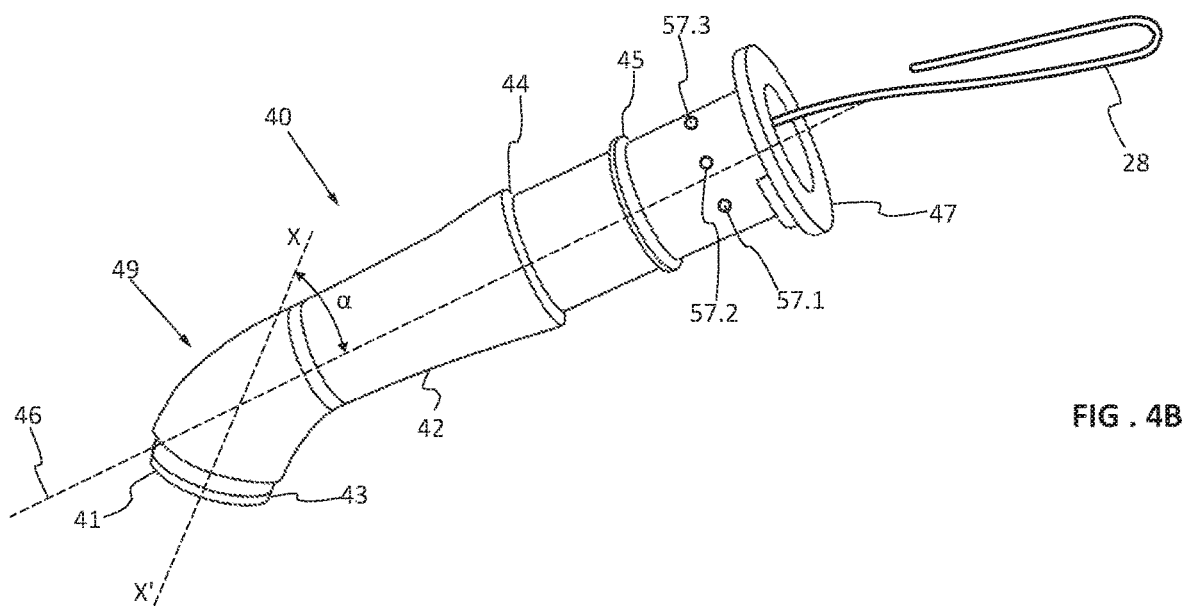
FIG. 4B is a perspective view of the optical waveguide provided with an overmolding.

In one particularly advantageous embodiment illustrated in FIGS. 4A and 4B, the hollow longitudinal body 40 is composed of an optical waveguide 41 and an overmolding 42 surrounding the optical waveguide 41. Consequently, the optical waveguide 41 and the overmolding 42 include a distal end corresponding to the distal end 49 of the hollow body 40, and a proximal end corresponding to the proximal end 48 of the hollow body 40.

The optical waveguide 41 allows guiding the light from the light source 21 from the proximal end 48 to the distal end 49 to illuminate a tooth surface to be analyzed. In parallel, the passage 29, which extends from the proximal end 48 to the distal end 49 of the hollow body, allows the passage of a cable 28 for transmission of data taken by the acquisition means to a data processing unit.

The overmolding 42 includes a set of units distributed along its outer surface and configured to allow, on the one hand, fixing the tip 26 on the extremity 49B of the distal end 49 of the overmolding 42, and, on the other hand, mounting the proximal end 48 in the housing 11 by means of the orientation assembly 50.

The units form, at a distal end of overmolding 42, a clipping unit 43. The tip 26 comprises a complementary clipping unit 26A. The two units 43 and 26A cooperate together to ensure the fixing of the movable tip 26 of the optical waveguide. The removable tip 26, which can be sterilized and has a time-restricted use, can thus be very easily manually mounted or removed on/from the body 40.

Advantageously, the units form a first thickened portion forming a first annular shoulder 44 and a second thickened portion 45 forming a second annular shoulder 45. The first thickened portion 44 forms an abutment against which an end 14 of the housing 11 comes to rest. The second thickened portion 45 forms an axial positioning abutment for the body 40 when the proximal end 48 is mounted in the cavity 53 formed by the two half-shells 51, 52.

Advantageously, the units also form a plurality of slots 57.1-57.7 formed on the outer surface of the overmolding 42, at the proximal end 48 of the overmolding 42. These slots are designed to cooperate with the radially projecting surface on the inner surface of the cavity 53 to ensure different angular positions of the measuring head 20 relative to the housing 11.

Figure 3:
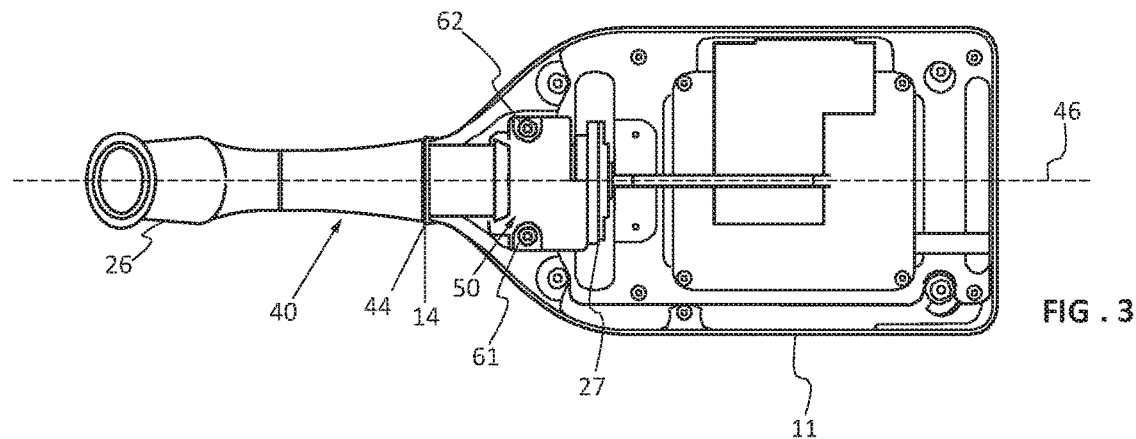
FIG. 3 is a bottom view in section of the housing of the device of FIG. 1.

Thus, when the measuring head is mounted in the housing 11, as illustrated in FIG. 3, one end of the housing 14 bears against the annular shoulder 44 of the overmolding 42. In addition, the proximal end 48 is held in position in the cavity 53 formed by the two half-shells which are fixed in a slot of the housing 11.

Preferably, the optical waveguide and the overmolding 42 are made of a lower refractive material than the material of the optical waveguide so as not to degrade the guiding conditions of the light. As an example, the optical waveguide is made of polymethylmethacrylate (PMMA) and the overmolding is made of polytetrafuoroethylene (PTFE).

Preferably, the optical waveguide 41 and the overmolding 42 are isolated from the outside by a metal coating to ensure proper guiding of the illumination light and the insulation of the outer light guide.

The faces of the guide can be machined to generate units designed to optimize the illumination at the output of the guide.

In known manner, the image acquisition means comprises a sensor 24 and an optical system 22.

The sensor 24 is, for example, a sensor provided with a pixel array so as to provide a signal for rendering an image of the tooth or a portion of the tooth. The sensor is preferably a field effect sensor. The sensor is connected to a data processing unit.

The illumination source 21 is fixed on a mounting bracket 27. The mounting bracket 27 is adapted to be positioned on a mounting surface 47 formed on the extremity 48B of the proximal end 48 of the overmolding 42.

Preferably, the bracket 27 also comprises a data processing unit and a control board of the light source. This board can also be offset on another electronic board associated with the display electronics.

Preferably, the illumination source comprises at least one white light-emitting diode and LED light-emitting diodes, whose wavelengths range between 448 and 630 nm, attached to the mounting bracket 27.

According to an advantageous embodiment of the invention, the LEDs, the control board and the optical system are integral with the overmolding 42. Thanks to this specific configuration, the sensor always sees the same distribution for a given LED. Thus, whatever the orientation of the body or of the optical waveguide 41, the illuminating beam on the tooth surface to be analyzed is always the same.

The use of an optical waveguide for conveying the light of the LEDS to a surface to be analyzed allows deporting the illumination sources while providing the most homogeneous possible illumination on the surface to be analyzed and this, regardless of the LED used and the orientation of the measuring head relative to the housing.

The optical system 22 includes a lens 25 and polarizing filters 23.

Mounting is achieved by setting the sensor 24 on a support piece 24.1 that receives an immobilizing lock 30. The lens 25 is screwed to the support piece 24.1 by a very fine thread to adjust the focal distance very accurately.

The support piece 24.1 with its sensor and bearing the lens 25 is introduced into the optical waveguide 29 and secured by any means, particularly by bonding.

Figure 5A:
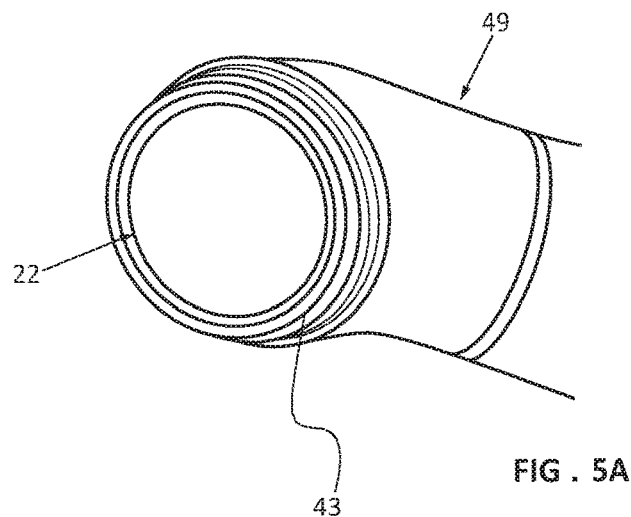
FIG. 5A illustrates a perspective view of the bent distal end of the hollow body, the tip of the distal end being provided with image acquisition means.
Figure 5B:
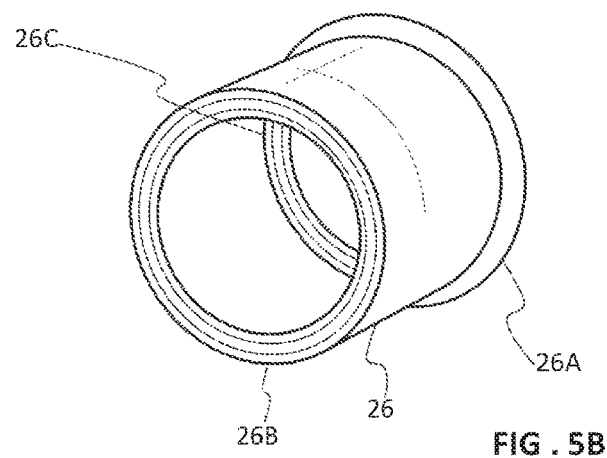
FIG. 5B illustrates a perspective view of the tip of the measuring head.
Figure 5C:
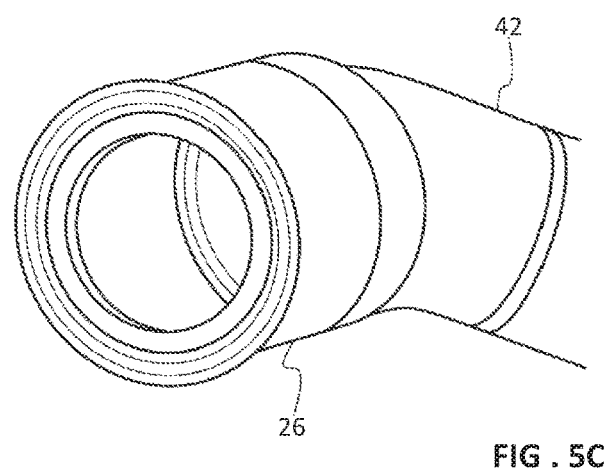
FIG. 5C illustrates a perspective view of the tip attached to the extremity of the bent distal end of the hollow body.

According to an advantageous embodiment illustrated in FIG. 5, the optical system 22 includes polarizing filters 23 positioned near the distal end 26A of the tip 26. These filters allow eliminating the light reflected by the surface to be analyzed.

According to one embodiment of the device, a first glass slide and a second glass slide maintain sandwiched a first polarizing filter 23 for the emitting part and a second filter 23 for the receiving part. The two slides and the two rectilinear polarizing filters, arranged so that their polarization axes are orthogonal, form a disk 23 having a diameter of 16 mm.

According to one embodiment, this disk 23 is attached by bonding to a glass slide which is clipped onto the end of the guide, or alternatively, the disk 23 is glued directly to the extremity 49B of the distal end 49 of the overmolding 42, as shown in FIG. 5A.

FIG. 5B shows in more detail the tip 26 that has a substantially tubular shape. This tip is made of a material having an opaque color. This tip is configured to be fixed on the extremity 49B of the distal end 49 of the overmolding 42. The tip 26 comprises a distal end 26A intended to come in contact with the tooth and a proximal end 26B positioned near the image acquisition means. Advantageously, the distal end 26A is separated from the proximal end 26B by a predetermined distance corresponding to a working distance to acquire an image. According to another advantage, the use of this tip allows eliminating stray light in the vicinity of the analyzed tooth. In addition, the tip allows precise positioning of the measuring head.

The proximal end 26B of the tip 26 comprises on its inner surface a clipping unit 26C that cooperates with a clipping unit 43 formed at the distal end 49 of the overmolding 42 for securing the tip on the body. The tip, which is for single use, can be manually mounted or removed very simply on/from the hollow body.

Figure 6:
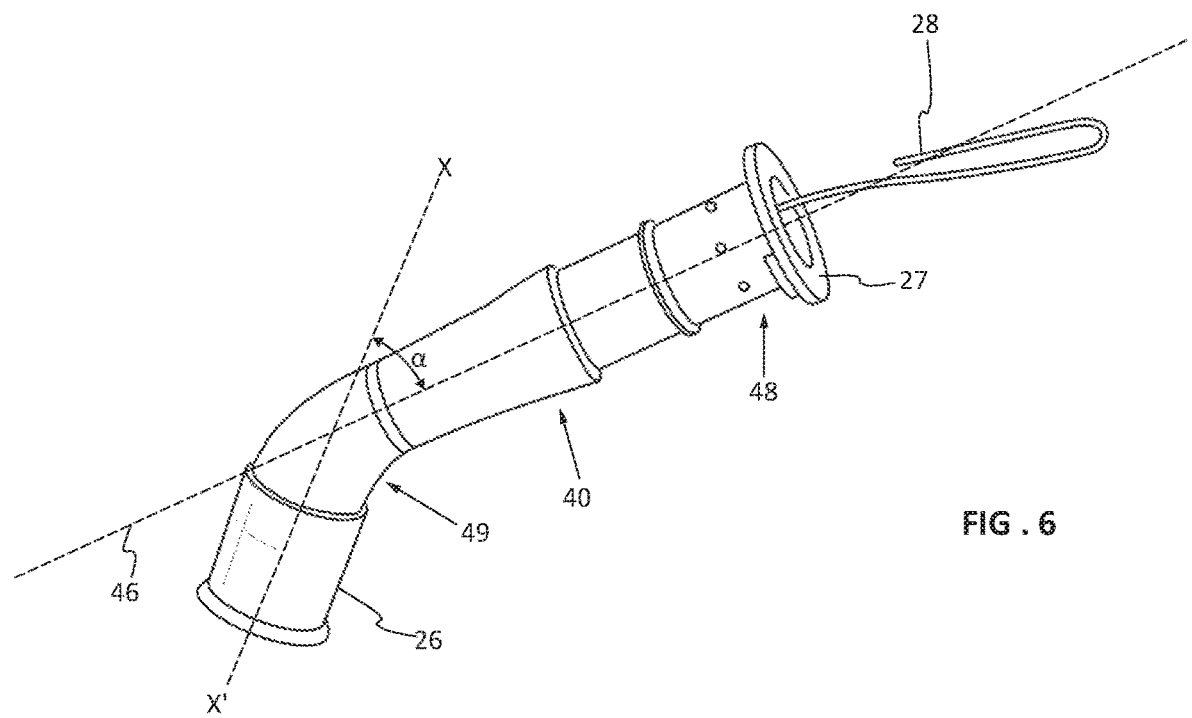
FIG. 6 is a view of the measuring head of FIG. 2 in an assembled configuration.

Preferably, the tip is in the form of a disposable cap having a tubular shape which extends the bent distal end 49 of the overmolding. As such, the tip has an angle of inclination α relative to the longitudinal axis 46 of the body 40 when attached to the latter. (See FIG. 6.)

According to another important feature, this tip includes a chromatic reference surface which allows the measuring device to perform an automatic self-calibration.

The practitioner can therefore hold the device that has just been described and receive data on the tooth before proceeding with its sizing and/or caring and/or preparing.

Processing the measured data allows determining the color of the tooth by areas, for example three areas. The self-calibration provides a comparison from a same reference, regardless of the device being used. The dental technician knows then which are the areas and which color to attribute to each of said areas so as not to have a uniform prosthesis whose aesthetic appearance would be unacceptable.

In addition, the practitioner can also take a complementary photo to scan the environment of the tooth or teeth affected by the seating of a prosthesis. To this end, an application can be developed in conjunction with the data and customer information processing software to introduce these complementary photos. Advantageously, the integration of photos into a file and their addition to the transmitted data will be automatically executed so that the practitioner does not have to worry about it, the practitioner needing only to open the patient's record.

It is indeed important to provide the dental technician, in addition to shade, brightness and translucency, parameters such as a color photo of the tooth whenever possible, photos of context i.e. a photo of the face, of the smile and photos with spacers more or less close to the reference tooth, or even the type of the stump and color of the stump used.

Figure 8:
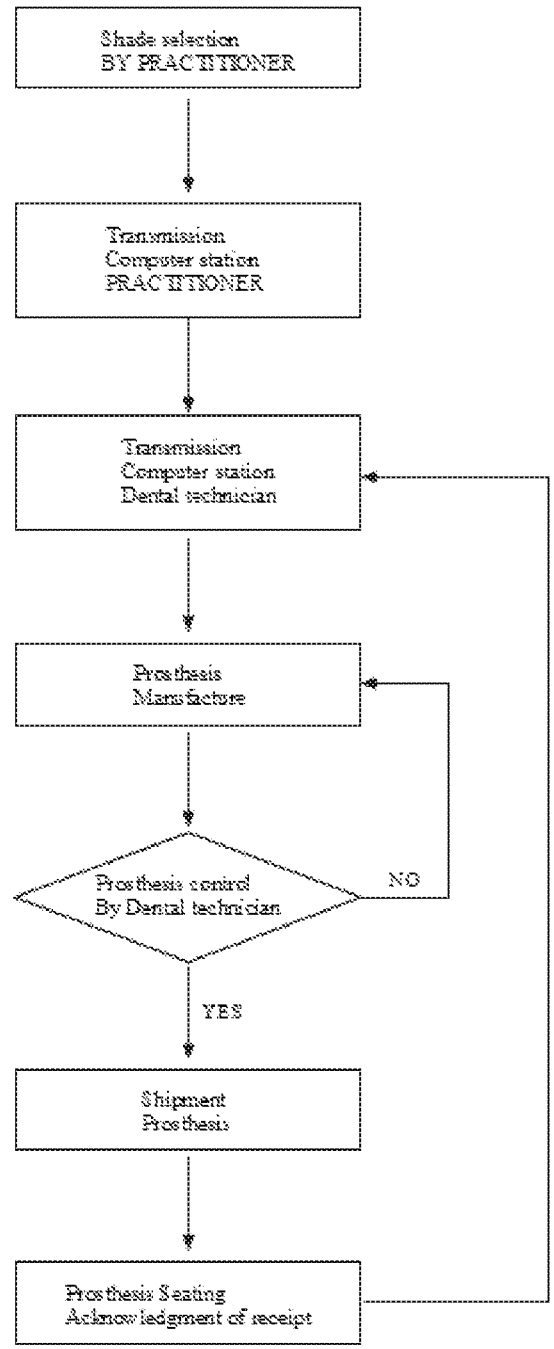
FIG. 8 shows a block diagram of the method for manufacturing and controlling of the present invention, in the simple case of a practitioner and a dental technician.

The method of the invention consists, as shown schematically in the block diagram of FIG. 8, in following the sequence of the following steps:

a) selecting the shade of the client's tooth to be replaced or restored by the practitioner using a color imaging device belonging to the practitioner, called DPraticien with local storage of such data, b) transmitting these data to a computer station in the practitioner's office which is equipped with software for the visualization of the measurement data and possibly with software for the entry of the client's contact information and specific data, both software programs being advantageously combined, c) transmitting these data to the computer station of a given dental technician, d) manufacturing the prosthesis according to the data received from the practitioner, e) controlling the data of the prosthesis manufactured by the dental technician using a shade selecting device identical to that belonging to said dental technician, called DProthesiste, calibrated in the same way as the DPraticien device of the practitioner, f) sending of the compliant prosthesis by the dental technician to the practitioner.

The method includes an additional step of transmitting, from the dental technician to the practitioner this time, the data of the manufactured prosthesis, as measured with said DProthesiste, prior to sending said prosthesis, its shipment occurring only if the practitioner gives his confirmation. The method becomes:

a) selecting the shade of the client's tooth to be replaced or restored by the practitioner using the DPraticien,
b) transmitting these data to the practitioner's computer station,
c) transmitting these data from the practitioner's computer station to the computer station of the dental technician,
d) manufacturing the prosthesis according to the data received from the practitioner,
e) controlling the data of the prosthesis manufactured using the DProthesiste,
f) transmitting the data of the manufactured prosthesis to the practitioner for his approval, and
g) sending of the compliant prosthesis by the dental technician to the practitioner after said practitioner's approval.

Figure 9:
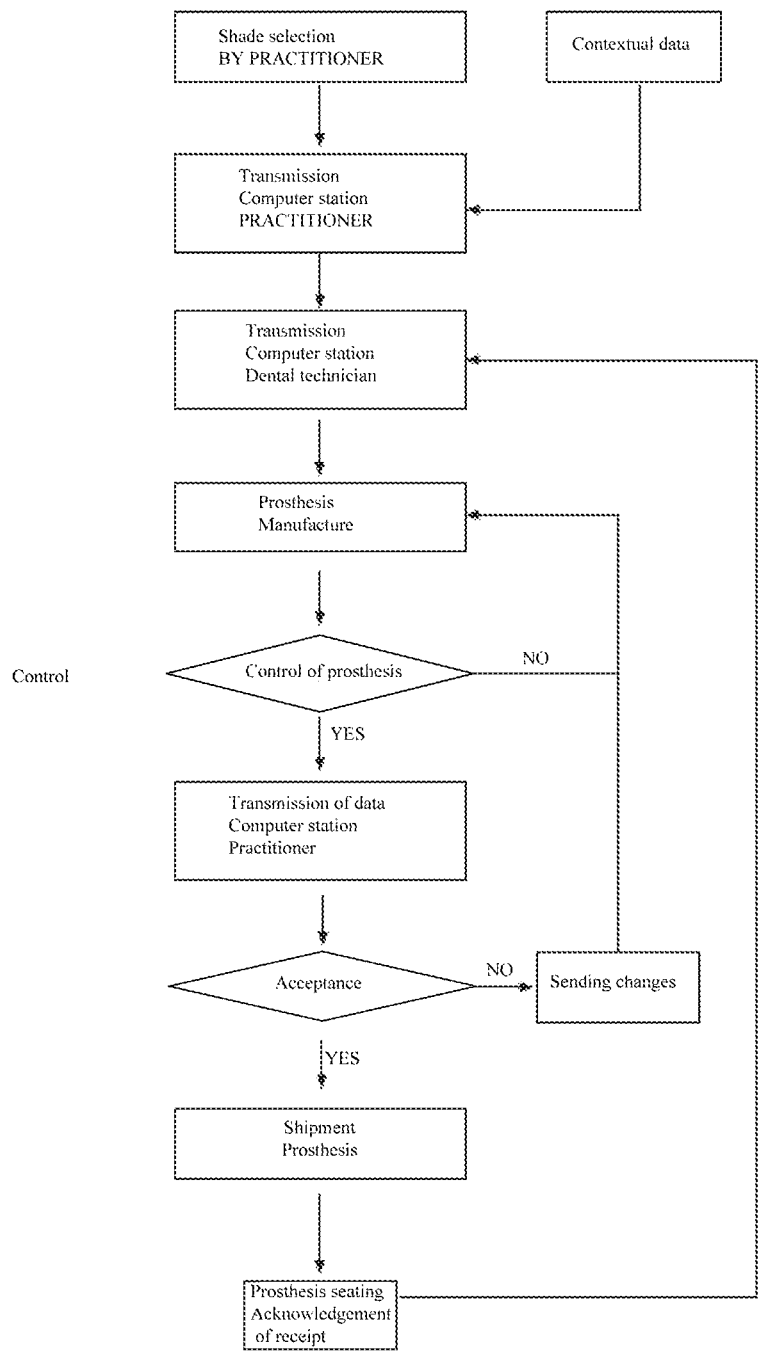
FIG. 9 shows a block diagram of the method for manufacturing and controlling of the present invention, in the case of a practitioner, a dental technician and a delocalized laboratory.

The invention also allows the practitioner to send amendments before giving his approval for the shipment of the prosthesis, see FIG. 9. In this case, the block diagram becomes the following:

a) selecting the shade of the client's tooth to be replaced or restored by the practitioner using the DPraticien,
b) transmitting these data to the practitioner's computer station,
c) transmitting these data from the practitioner's computer station to the computer station of the dental technician,
d) manufacturing the prosthesis according to the data received from the practitioner,
e) controlling the data of the prosthesis manufactured using the DProthesiste,
f) transmitting the data of the manufactured prosthesis to the practitioner for his approval,
g) transmitting data changes by the practitioner,
h) changes made to the prosthesis by the dental technician according to these data changes,
i) controlling the data of the prosthesis manufactured using the DProthesiste,
j) transmitting data of the modified prosthesis by the dental technician to the practitioner for approval by the practitioner, and
k) sending of the compliant prosthesis by the dental technician to the practitioner after said practitioner's approval.

The device for selecting the shade of the tooth for all the steps of the method, both the DPraticien and the DProthesiste, is advantageously the device which was described above in the present invention and which comprises a swivel head, which allows selecting a much more precise shade by orienting the head of said device on said tooth followed by a measurement of said tooth parameters.

The method also provides that, notwithstanding the quality of the exchanges of the data obtained, the practitioner make corrections, which may be related to his expertise, to the manufactured prosthesis whose data have been transmitted. Therefore, the dental technician can make changes before submitting new data on the modified prosthesis and sending the finalized prosthesis after confirmation of compliance by the practitioner.

The method of the invention allows solving the problem raised, namely the quality control of the prosthesis by the dental technician before he sends it to the practitioner, based on measured parameters identical to the parameters measured by the practitioner.

In all cases, once the prosthesis is seated, the practitioner returns to the management software to perform the seating and compliance control, the dental technician being informed of this seating.

The practitioner can also add comments, if necessary, to ensure accurate feedback to the dental technician concerned, or make a comment on a dedicated community forum.

It is also possible to use the cloud technology for the transfer of data that represent bulky files, which is simply a virtual server. This type of virtual communication and servers or IT are perfectly included in the method according to the invention.

The method also allows completing the data on the tooth or teeth involved at any time with data from the peripheral dental context of the tooth or teeth concerned. Such contextual data can be digital photos as described above, data on the material to be used or even the trademark of the ceramic powder, etc.

The invention claimed is:

1. A method for manufacturing and controlling the conformity of a dental prosthesis from parameters obtained intra-orally with a first shade selecting device characterized in that it comprises the following steps:
   a) selecting the shade of a client tooth to be replaced or restored by the practitioner using the first shade selecting device belonging to the practitioner with local storage of first data,
   b) transmitting the first data to a computer station of the practitioner which is equipped with software for the visualization of the measurement data and with software for the entry of the client's contact information and specific data, both software programs being advantageously combined,
   c) transmitting the first data to a computer station of a dental technician,
   d) manufacturing the prosthesis according to the first data received from the practitioner,
   e) capturing second data of the prosthesis manufactured by the dental technician using a second shade selecting device belonging to said dental technician that is identical to and calibrated in the same way as the first shade selecting device of the practitioner,
   f) transmitting the second data of the manufactured prosthesis to the practitioner for approval, and
   g) sending of the compliant prosthesis by the dental technician to the practitioner after said practitioner's approval
   wherein each of the first and second shade selecting devices comprises a measuring head including at least a tip, one light source and image acquisition means, and a data processing unit,
   wherein each of the data processing units allows determining the color of the tooth by areas to achieve a mapping of variations in different characteristics of the tooth, and
   wherein each of the tips includes a chromatic reference surface which allows the first and second shade selecting devices to perform an automatic self-calibration, the chromatic reference surface being identical in both first and second shade selecting devices.

2. The method for manufacturing and controlling the conformity of a dental prosthesis according to claim 1, characterized in that it comprises the following steps:
   h) transmitting data changes by the practitioner, i) changing the prosthesis by the dental technician according to these data changes,
j) capturing third data of the modified prosthesis manufactured using the second shade selecting device,
k) transmitting the third data of the modified prosthesis by the dental technician to the practitioner for approval by the practitioner, and
l) sending of the compliant modified prosthesis by the dental technician to the practitioner after said practitioner's approval.

3. The method for manufacturing and controlling the conformity of a dental prosthesis according to claim 1, characterized in that the first shade selection device and the second shade selection device each comprises a housing, a handle and the measuring head provided with the tip intended to come into contact with the tooth surface to be analyzed, as well as an orientation assembly allowing the measuring head to occupy different angular positions relative to the housing.

4. The method for manufacturing and controlling the conformity of a dental prosthesis according to claim 1, characterized in that the first transmitted data includes contextual data including: a photo of the face and/or smile and photos with spacers more or less close to the reference tooth or also the type of stump and/or the color of the stump used.

* * * * *